(12) United States Patent
Raviv et al.

(10) Patent No.: US 10,173,056 B2
(45) Date of Patent: Jan. 8, 2019

(54) METHODS FOR IMPROVING MALE FERTILITY

(71) Applicant: Tel Hashomer Medical Research Infrastructure and Service Ltd., Tel Hashomer (IL)

(72) Inventors: Gil Raviv, Ganie Tikva (IL); David Shashar, Ramat Gan (IL); Yoram Shadmi, Ramat Gan (IL); Itzchak Shvitlowsky, Shomam (IL); David Castel, Tel Aviv (IL)

(73) Assignee: Tel Hashomer Medical Research Infrastructure and Service Ltd., Ramat Gan (IL)

( * ) Notice: Subject to any disclaimer, the term of this patent is extended or adjusted under 35 U.S.C. 154(b) by 74 days.

(21) Appl. No.: 14/413,898

(22) PCT Filed: Jul. 11, 2013

(86) PCT No.: PCT/IL2013/050594
§ 371 (c)(1),
(2) Date: Jan. 9, 2015

(87) PCT Pub. No.: WO2014/009960
PCT Pub. Date: Jan. 16, 2014

(65) Prior Publication Data
US 2015/0190632 A1 Jul. 9, 2015

Related U.S. Application Data

(60) Provisional application No. 61/741,037, filed on Jul. 11, 2012.

(51) Int. Cl.
*A61N 1/20* (2006.01)
*A61N 1/36* (2006.01)
(Continued)

(52) U.S. Cl.
CPC ............ *A61N 1/205* (2013.01); *A61B 5/4387* (2013.01); *A61B 5/4836* (2013.01);
(Continued)

(58) Field of Classification Search
CPC .. A61N 1/205; A61N 1/0408; A61N 1/36002; A61N 1/0492; A61B 10/0058;
(Continued)

(56) References Cited

U.S. PATENT DOCUMENTS 5,454,840 A * 10/1995 Krakovsky ............... A61F 2/26
607/39
5,571,118 A    11/1996 Boutos
(Continued)

FOREIGN PATENT DOCUMENTS

EP    2258443    12/2010

OTHER PUBLICATIONS

Herrick,John Semen Collection by Electrical Stimulation, (1955) Iowa State University Veterinarian: vol. 17:Iss.3,Article 4.*
(Continued)

*Primary Examiner* — Christopher D Koharski
*Assistant Examiner* — Roland Dinga
(74) *Attorney, Agent, or Firm* — Knobbe, Martens, Olson & Bear, LLP

(57) ABSTRACT

The present invention is directed to methods for improving male fertility inter alia by increasing sperm count in a male subject. The methods of the invention comprise applying a positive electrical current below sensation level to at least one site of a scrotum of a subject in need thereof.

16 Claims, 3 Drawing Sheets

(51) Int. Cl.
*A61B 5/00* (2006.01)
*A61B 10/00* (2006.01)
*A61D 19/00* (2006.01)
*A61N 1/04* (2006.01)

(52) U.S. Cl.
CPC ......... *A61B 10/0058* (2013.01); *A61D 19/00* (2013.01); *A61N 1/0408* (2013.01); *A61N 1/36007* (2013.01); *A61B 2503/40* (2013.01); *A61N 1/0492* (2013.01); *F04C 2270/041* (2013.01)

(58) Field of Classification Search
CPC ... A61B 5/4836; A61B 5/4387; A61B 203/40; A61D 19/00; F04C 2270/041
USPC .......................................................... 607/39
See application file for complete search history.

(56) References Cited

U.S. PATENT DOCUMENTS

| | | | |
|---|---|---|---|
| 5,782,902 A | 7/1998 | Boutos | |
| 2013/0144357 A1* | 6/2013 | Forward | ............. A61N 1/0492 607/39 |

OTHER PUBLICATIONS

Brackett (2012) Infertility in men with spinal cord injury: research and treatment. Scientifica; 2012: 578257.
Brindley (1981) Electroejaculation: its technique, neurological implications and uses. J Neurology,Neurosurgery, and Psychiatry; 44(1): 9-18.
Chan et al., (2006) A simple zeta method for sperm selection based on membrane charge. Fertility and Sterility; 85(2): 481-486.
Ishijima et al., (1991) Zeta potential of human X- and Y-bearing sperm. Int J Andrology; 14(5): 340-347.
Kam et al., (2007) Retention of membrane charge attributes by cryopreserved-thawed sperm and zeta selection. J Assist Reprod Genet 24(9): 429-34.
Veres (1968) Negative electrical charge of the surface of bull sperm. Mikroskopie 23(5): 166-9.
Yamamoto et al., (1995) Bulk sperm collection by epididymal micropuncture and stimulation of the spermatic nerve; a novel method for sperm retrieval for IVF for surgically irreparable vasal obstruction. Int J Androl 18(2): 97-102.
Gui et al., (2004) Male hormonal contraception: suppression of spermatogenesis by injectable testosterone undecanoate alone or with levonorgestrel implants in chinese men. J Androl. Sep.-Oct. 2004;25(5):720-7.

* cited by examiner

METHODS FOR IMPROVING MALE FERTILITY

This application is the U.S. National Phase under 35 U.S.C. § 371 of International Application No. PCT/IL2013/050594, filed Jul. 11, 2013, designating the U.S., and published in English as WO 2014/009960 on Jan. 16, 2014, which claims priority to U.S. Provisional Patent Application 61/741,037 filed Jul. 11, 2012, the entire contents of which are incorporated herein by reference.

FIELD OF THE INVENTION

The present invention is directed to methods for improving male fertility inter alia by increasing sperm count in a male subject. The methods of the invention comprise applying a positive electrical current below sensation level to at least one site of a scrotum of a subject in need thereof.

BACKGROUND OF THE INVENTION

Male infertility commonly refers to the inability of a male to induce pregnancy in a fertile female after a period of 12 months. Male infertility represents approximately 40% of couple infertility causes. Most of male infertility cases are due to sperm abnormalities caused by a range of conditions, such as, anatomical problems, hormonal imbalances, genetic defects and idiopathic cases.

Sperm abnormalities are categorized as an abnormal sperm production with shape or motile defects, abnormal low sperm number (oligospermia) or seemingly without any sperm (azoospermia).

Treatment of male infertility depends on the underlying medical conditions that cause the fertility problem. For example, drug therapy may be used to treat hormonal disorders while surgery may be conducted in cases of obstruction in the reproductive tract. When treatment does not remedy the infertile condition, Assisted Reproductive Techniques (ARTs), such as, In Vitro Fertilization (IVF) and Intracytoplasmic Sperm Injection (ICSI), are applied. ICSI may involve obtaining semen through invasive procedures, which include Testicular Sperm Aspiration (TESA), Testicular Sperm Extraction (TESE), Percutaneous Epididymal Sperm Aspiration (PESA) or Microsurgical Epididymal Sperm Aspiration (MESA).

Previous studies show that mature sperm membranes possess a negative electrical charge between −16 mV to −20 mV, often termed zeta potential or electrokinetic potential. Further studies show different values of zeta potential for Y-bearing and X-bearing sperm being approximately −16 mV and approximately −20 mV, respectively (Ishijima S A et al., Int. J. Androl., 14 (1991), pp. 340-347). This difference in the electrical charge characteristics between the Y and X-bearing was utilized for selection of sperm according to morphology and kinematic parameters and was associated with increased fertilization and pregnancy after assisted reproduction procedures.

U.S. Patent Application, Publication No. 2013/0144357, discloses a device for increasing endogenous production of testosterone in a subject. The device includes a first electrode, a second electrode and a power source. The first electrode is configured to contact the skin in the pubic region of the subject. The power source is configured to deliver about 6 volts or corresponding to amperage between about 0.001 amps to about 0.003 amps.

There is an unmet need for advantageous techniques for improving male fertility and sperm reproductive capacity.

SUMMARY OF THE INVENTION

The present invention is directed to methods for improving male fertility, including, but not limited to, increasing spermatocytes count and increasing sperm quality in a male subject. The method of the invention comprise applying a positive direct current (DC) electrical current below the sensation level, namely, of no more than 1,000 µA to at least one site on a scrotum of a subject in need thereof. The method is particularly useful for inducing or improving male fertility.

The invention is based in part on the unexpected discovery that applying low positive electrical current, in the order of microampers (µA), and no more than 1,000 µA to the scrotum of a subject, increases significantly the sperm count and quality in said subject. Surprisingly, the method of the invention increases spermatocytes production while applying an electric field which does not reach sensation level and is too weak to cause classical nerve stimulation. Advantageously, the effective electrical current according to the invention is safe and furthermore does not cause any obnoxious feeling, such as, pain or otherwise unpleasant or irritating sensation.

Without being bound by any theory or mechanism of action, sperm known to possess an electric charge of between −16 mV to −20 mV attracts to positive electrical current. Accordingly, sperm passing through the seminiferous tubules is concentrated and immobilized in locations adjacent to the place where a positive electrical current is applied. Hence, the method of the invention may be utilized for obtaining semen sample enriched with highly productive sperm which is suitable for assisted reproductive techniques.

Moreover, the method of the present invention offers higher probability of success in spontaneous intercourse among men with normal sperm count.

According to a first aspect, the present invention provides a method for improving male fertility, comprising applying a positive DC current to at least one site of the scrotum of a male subject in need thereof, said current is within the range of 1 to 1000 µA.

According to another aspect, the present invention provides an assisted reproductive method comprising:
applying a positive DC current to at least one site of the scrotum of a male subject in need thereof, said current is within the range of 1 to 1000 µA;
obtaining at least one sperm sample from said subject; and
performing an assisted reproductive technique using said sample or a fraction thereof.

According to yet another aspect, the present invention provides a method for improving male fertility, consisting of applying a positive DC current to at least one site of the scrotum of a male subject in need thereof, said current is within the range of 1 to 1,000 µA.

According to yet another aspect, the present invention provides an assisted reproductive method consisting of:
applying a positive current to at least one site of the scrotum of a male subject in need thereof, said current is within the range of 1 to 1000 µA;
obtaining a sperm at least one sample from said subject; and
performing an assisted reproductive technique using said sample or a fraction thereof.

According to some embodiments, the positive current is delivered in intervals.

According to some embodiments, the positive current is delivered in pulses.

According to some embodiments, said at least one sperm sample is obtained from a testis or epididymis of said male subject.

According to some embodiments, said at least one sperm sample is obtained via ejaculation.

According to some embodiments, said at least one sperm sample is obtained during treatment. According to some embodiments, said at least one sperm sample is obtained post treatment. According to some embodiments, said at least one sample is obtained at most 74 days post treatment. According to some embodiments, said at least one sample comprises a plurality of samples.

As used herein, the term 'treatment' refers to applying a positive electrical current.

According to some embodiments, said positive electrical current is continuous.

According to some embodiments, said positive electrical current is at most 1,000 µA. According to some embodiments, said positive electrical current is at most 800 µA. According to some embodiments, said positive electrical current is at most 600 µA. According to some embodiments, said positive electrical current is within the range of 1 µA to 999 µA. According to some embodiments, said positive electrical current is within the range of 10 µA to 999 µA. According to some embodiments, said positive electrical current is within the range of 20 µAm to 1,000 µAm, 10 µA to 800 µA, 20 µA to 800 µA, 10 µA to 600 µA, 20 µA to 600 µA, 10 µA to 500 µA, 10 µA to 400 µA, 10 µA to 300 µA, 10 µA to 200 µA. Each possibility is a separate embodiment of the invention.

According to some embodiments, said positive electrical current is about 40 µA. According to some embodiments, said positive electrical current is about 100 µA.

According to some embodiments, said positive electrical current is within the range of 10 to 250 µA.

According to some embodiments, said positive electrical current is within the range of 20 to 120 µA.

According to some embodiments, applying a positive current to at least one site of the scrotum comprises contacting said at least one site with at least one positive electrode.

According to some embodiments, said at least one positive electrode comprises a plurality of positive electrodes.

According to some embodiments, said at least one site is an external site.

According to some embodiments, said at least one site is an external site in close proximity to the rete tesis.

According to some embodiments, said applying is carried out for at least 12 hours. According to some embodiments, said applying is carried out for at least 24 hours. According to some embodiments, said applying is carried out for at least 72 hours. According to some embodiments, said applying is carried out for at least 7 days. According to some embodiments, said applying is carried out for at least 14 days. According to some embodiments, said applying is carried out for at least 21 days. According to some embodiments, said applying is carried out for at least 30 days. According to some embodiments, said applying is carried out for at least 45 days. According to some embodiments, said applying is carried out for at least 60 days. According to some embodiments, said applying is carried out for at most 74 days. According to some embodiments, said applying is carried out for 10 to 74 days.

According to some embodiments, the method further comprises obtaining a semen sample from said subject.

According to some embodiments, said semen sample is obtained from the testis, epididymis or ejaculation.

According to some embodiments, said semen sample is derived from a location at the vicinity of said at least one site.

According to some embodiments, obtaining is carried out by aspiration or extraction.

According to some embodiments, aspiration is carried out via a procedure selected from the group consisting of: Testicular Sperm Aspiration (TESA), Microsurgical Epididymal Sperm Aspiration (MESA), Percutaneous Epididymal Sperm Aspiration (PESA) and Testicular Fine Needle Aspiration (TEFNA).

According to some embodiments, extraction is carried out via Testicular Sperm Extraction (TESE).

According to some embodiments, said sample comprises spermatozoa, spermatid or a combination thereof.

According to some embodiments, the method further comprises determining infertility in said male subject, and applying said positive current to at least one site of the scrotum of a male having an infertility condition.

According to some embodiments, determining infertility comprises determining sperm characteristics selected from the group consisting of: total sperm count, sperm concentration, ejaculate volume, sperm motility, sperm morphology and sperm viability. Each possibility is a separate embodiment of the invention.

According to some embodiments, improving male fertility comprises one or more of increasing sperm count and improving sperm reproductive capacity.

According to some embodiments, said infertility condition is selected from the group consisting of: oligozoospermia, astenozoospermia, teratozoospermia and azoospermia. Each possibility is a separate embodiment of the invention.

According to some embodiments, said male subject is infertile or subfertile.

According to some embodiments, said male subject has a normal sperm count.

According to some embodiments, said male subject has a normal sperm count and sperm quality.

According to some embodiments, said assisted reproductive technology is selected from the group consisting of: intrauterine insemination (IUI), in vitro fertilization (IVF), intracytoplasmic sperm injection (ICSI) and cryopreservation. Each possibility is a separate embodiment of the invention.

According to yet another aspect, the present invention provides use of a positive DC electrical current according to the embodiments of the invention for increasing spermatocytes count in a subject in need thereof.

According to some embodiments, the present invention provides a positive DC current within the range of 1 to 1,000 µA for use in applying to at least one site of the scrotum of a male subject in need thereof, thereby improving male fertility.

According to some embodiments, the present invention provides a positive DC current within the range of 1 to 1,000 µA for improving male fertility via applying said positive DC current to at least one site of the scrotum of a male subject in need thereof, thereby.

According to some embodiments, the present invention provides a positive DC current within the range of 1 to 1,000 µA for applying to at least one site of the scrotum of a male subject in need thereof, thereby improving male fertility.

According to some embodiments, said applying comprises externally applying said positive DC current to at least one site of the scrotum of said male subject.

According to some embodiments, said applying comprises externally applying a positive electrode on at least one site of the scrotum of said male subject. According to some embodiments, the positive electrode comprises a plurality of electrodes.

According to some embodiments, the present invention provides a positive DC current within the range of 1 to 1,000 µA for assisted reproductive techniques.

According to some embodiments, the positive current is delivered in intervals or in pulses. Each possibility is a separate embodiment of the invention.

According to some embodiments, said positive electrical current is continuous.

According to some embodiments, said positive electrical current is within the range of 1 µAm to 1000 µAm. According to some embodiments, said positive electrical current is at most 1000 µA. According to some embodiments, said positive electrical current is at most 800 µA. According to some embodiments, said positive electrical current is at most 600 µA. According to some embodiments, said positive electrical current is within the range of 1 µA to 999 µA. According to some embodiments, said positive electrical current is within the range of 10 µA to 999 µA. According to some embodiments, said positive electrical current is within the range of 10 µA to 800 µA, 20 µA to 800 µA, 10 µA to 600 µA, 20 µA to 600 µA, 10 µA to 500 µA, 10 µA to 400 µA, 10 µA to 300 µA, 10 µA to 200 µA. Each possibility is a separate embodiment of the invention.

According to some embodiments, applying a positive current to at least one site of the scrotum comprises contacting said at least one site with a positive electrode.

According to some embodiments, said at least one site is an external site in close proximity to the rete tesis.

According to some embodiments, said applying is carried out for at least 12 hours, for at least 24 hours, for at least 72 hours, for at least 7 days, for at least 14 days, for at least 21 days, for at least 30 days, for at least 45 days, for at least 60 days or for at least 74 days. Each possibility is a separate embodiment of the invention.

According to some embodiments, the present invention provides a kit comprising a first component capable of applying an external positive electric current to at least one site of the scrotum of a male subject, said current is within the range of 1 µA to 1,000 µA, thereby improving fertility of said male subject.

According to some embodiments, the kit further comprises a second component capable of regulating, monitoring and/or adjusting the positive electrical current.

According to some embodiments, the kit further comprises instructions for use of said first component for improving fertility in a male subject.

According to some embodiments, the means capable of applying a positive electrical current to at least one site of the scrotum of a male subject, comprises a pair of electrodes and a power source.

According to some embodiments, said means capable of applying a positive electrical current to at least one site of the scrotum of a male subject, comprises at least one positive electrode, at least one negative electrode and a power source.

According to some embodiments, said means capable of applying a positive electrical current to at least one site of the scrotum of a male subject, comprises a plurality of positive electrodes, a plurality of negative electrodes and a power source.

According to some embodiments, the means capable of applying a positive electrical current is capable of applying the positive current in a continuous form, in intervals and/or pulses.

According to some embodiments, the means capable of applying a positive electrical current is capable of applying a continuous positive current.

According to some embodiments, the means capable of applying a positive electrical current is capable of applying the positive current in intervals.

According to some embodiments, the means capable of applying a positive electrical current is capable of applying the positive current for at least 12 hours, for at least 24 hours, for at least 72 hours, for at least 7 days, for at least 14 days, for at least 21 days, for at least 30 days, for at least 45 days, for at least 60 days or for at most 74 days. According to some embodiments, said applying is carried out for 10 to 74 days.

According to some embodiments, the kit further comprises means for deriving a sperm sample from a subject.

According to some embodiments, the kit further comprises means for deriving a sperm sample from a subject by aspiration or extraction.

According to some embodiments, the kit further comprises means for determining a sperm characteristics selected from the group consisting of: total sperm count, sperm concentration, ejaculate volume, sperm motility, sperm morphology and sperm viability.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
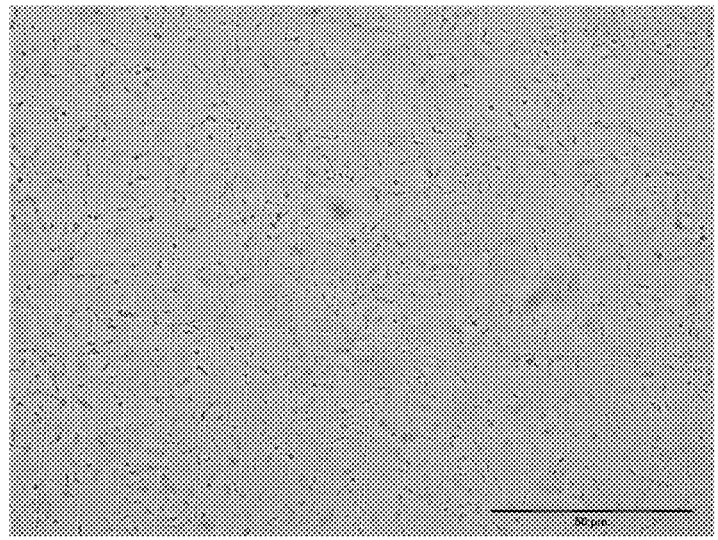
FIGS. 1A and 1B are micrographs of sperm samples obtained from male pigs from control epedidymis not subjected to positive electric current (1A) and from epididymis after treatment with a positive electric current of 40 µAm (1B) to the testis.
Figure 1B:
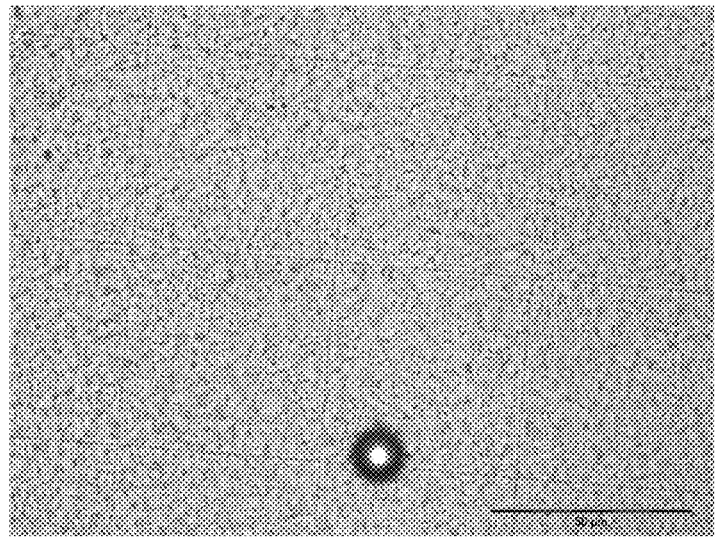

The present invention relates to methods for inducing or improving male fertility, comprising increasing the total sperm count and/or improving the reproductive performance of semen of male subjects. The methods involve applying a low electrical current, of no more than 1000 microampere, to one or more sites on the scrotum of a subject in need thereof. The invention is useful for healthy men with normal sperm count as well as for men with abnormal semen quality and/or count and may be utilized to obtain a highly productive sperm sample of a male subject for subsequent performance in an assisted reproductive technique or for improving induction of pregnancy via natural intercourse.

According to some embodiments, the present invention provides a method for increasing sperm count, comprising applying a positive electrical current on at least one site on/at the scrotum of a subject in need thereof. The positive DC electrical current is within the range of 1 to 1,000 µA. According to some embodiments, said positive electrical current is at most 1000 µA. According to some embodiments, said positive electrical current is at most 800 µA. According to some embodiments, said positive electrical current is at most 600 µA. According to some embodiments, said positive electrical current is within the range of 1 µA to 999 µA. According to some embodiments, said positive electrical current is within the range of 10 µA to 999 µA. According to some embodiments, said positive electrical current is within the range of 10 µA to 800 µA, 20 µA to 800 µA, 10 µA to 600 µA, 20 µA to 600 µA, 10 µA to 500 µA, 10 µA to 400 µA, 10 µA to 300 µA, 10 µA to 200 µA. Each possibility is a separate embodiment of the invention.

According to some embodiments, said positive electrical current is about 40 µA. According to some embodiments, said positive electrical current is about 100 µA.

The term "about" as used herein refers to +/−10% of the indicated amount.

The method of the present invention may be applied in any mammal, including, but not limited to humans. The method is particularly suitable for treating human males, including human males with abnormal semen quality and/or count and males having a normal sperm count.

As used herein the terms "sperm" and "spermatocytes" are interchangeable and refer to the male reproductive cells. Sperm is created during the process of spermatogenesis. In this process, a diploid spermatogonium which resides in the basal compartment of seminiferous tubules, undergoes mitosis to produce two diploid intermediate cells called primary spermatocytes. Each primary spermatocyte then moves into the adluminal compartment of the seminiferous tubules and undergoes meiosis to produce two haploid secondary spermatocytes, which will later divide once more into haploid spermatids. These ultimately develop into mature spermatozoa. Non-motile spermatozoa are transported through the seminifreous tubules to the epididymis by testicular fluid secreted from the sertoli cells. In the epididymis the spermatozoa gain motility. In humans the process takes approximately 74 days. Spermatids as well as spermatozoa are both reproductive and capable of fertilizing an oocyte artificially in IVF and/or ICSI and spermatozoa are capable of fertilizing an oocyte spontaneously and artificially, such as, in an IUI, IVF or ICSI technique. Accordingly, in the context of the embodiments of the present invention, the term "sperm" comprises spermatids, spermatozoa or a combination thereof.

According to some embodiments, the method of the invention is useful in increasing sperm count and/or quality. Sperm count/quality is a measure of the ability of sperm to accomplish fertilization and accordingly it is a measure of fertility in a male.

Commonly, male infertility treatment is determined according to the cause of infertility. However, in many cases treatment does not remedy the infertile condition and thus, Assisted Reproductive Techniques (ARTs) are applied in an attempt to achieve pregnancy.

The terms "Assisted reproductive technology" or "ART" are interchangeable, and refer to methods or techniques for achieving pregnancy or intending to achieve pregnancy using artificial or partially artificial procedures. ART includes any artificial or partially artificial method or technology known in the art aimed to obtain pregnancy. According to some embodiments, ART is selected from the group consisting of: intrauterine insemination (IUI), in vitro fertilization (IVF) and intracytoplasmic sperm injection (ICSI).

One example of ART is intracytoplasmic sperm injection (ICSI) which involves injecting a single sperm into an oocyte and subsequent implanting the fertilized oocyte back into the woman's uterus. Success rates of ICSI vary according to etiology of infertility. In infertile conditions of oligospermia or azoospermia, ICSI requires obtaining semen. Sperm retrieval may be done by any one or more of the following techniques: Testicular Sperm Aspiration (TESA), Testicular Sperm Extraction (TESE), Testicular Fine Needle Aspiration (TEFNA), Percutaneous Epididymal Sperm Aspiration (PESA), Microsurgical Epididymal Sperm Aspiration (MESA) or via ejaculate.

TESA is associated with aspiration of semen sample by a syringe, while TESE involves extraction of small strips of testicular tissue. TESE is frequently accompanied with pain, tissue loss and reduced success in future TESE due to tissue scaring. Hence, even ART procedures combined or not with supportive techniques are not always successful and are associated with pain to patients.

The testicular fine needle aspiration (TEFNA) involves percutaneous puncture of the testis with a fine needle and aspiration with a syringe. This approach may enable the operator to reach more testicular sites, including those located within the testis, without causing extensive testicular damage and consequently with lesser side-effects.

Percutaneous epididymal sperm aspiration (PESA) refers to a technique for collecting sperm from the epididymis, a tube that carries sperm from the testicle to the vas deferens. The technique is based on needle aspiration and includes inserting a needle through the skin of the scrotum and retrieving sperm there from. This technique is effective in the event of a possible blockage of the vas deferens among other events.

Microsurgical Epididymal Sperm Aspiration (MESA) refers to retrieval of sperm containing fluid from optimal areas of the epididymis that are selected and sampled using high-power optical magnification provided by an operating microscope.

According to some embodiments, the method of the invention is effective in improving the reproductive capacity of the male's sperm in at least one of the sperm characteristics selected from the group consisting of: total sperm count, sperm concentration, ejaculate volume, sperm motility, sperm morphology and sperm viability. Each possibility represents a separate embodiment of the invention.

As used herein the term "sperm count" refers to the concentration of sperm in a sperm sample. In the western world, the normal average sperm count in humans is between 15 and 40 million sperm per milliliter. A lower sperm count is considered oligozoospermia, and azoospermia is the medical condition of a man not having any measurable level of sperm in his semen.

According to some embodiments, the method of the invention is effective in increasing the sperm count of a subject. According to some embodiments, the method of the invention is applied until maximum sperm count is obtained. This could be applied up to 74 days after treatment has ended. The sample may be taken during treatment, any time after completion of treatment, or up to 74 days after completion of treatment. A sample taken during treatment refers to one or more samples derived before treatment is completed. The samples may be analyzed in order to determine the duration of the treatment.

According to some embodiments, the sperm count may be increased by at least 1.2, 1.4, 1.6, 1.8 or 2 folds as compared to the sperm count of a subject not subjected to the positive electrical current according to the method of the invention. Each possibility represents a separate embodiment of the invention.

According to some embodiments, the sperm count of a subject may be increased by at least 2 folds, 4 folds, 10 folds, 15 folds and 20 folds as compared to the sperm count of a subject not subjected to the positive electrical current according to the method of the invention. Each possibility represents a separate embodiment of the invention.

Sperm count/quality may be assessed by any method known in the art. Typically, the diagnosis of male infertility relies on microscopic assays which assess sperm concentration, motility and morphology. Sperm count can also be estimated by kits that measure the amount of a sperm-associated protein. Sperm volume can be determined by measuring the weight of the sample. Computer Assisted Semen Analysis (CASA) is a catch-all phrase for automatic or semi-automatic semen analysis techniques. Most systems are based on image analysis, but alternative methods exist such as tracking cell movement on a digitizing tablet. CASA are most-often used for the assessment of sperm concentration and mobility characteristics, such as velocity and linear velocity. Further sperm tests include, but are not limited to, a Hamster zona-free ovum test for measuring ability of sperm to penetrate the oocyte, Sperm Chromatin Structure Assay (SCSA) for measuring DNA fragmentation or Hemizona for measuring binding capacity for the zona pellucida of the oocyte.

The positive electrical current may be delivered by any method or suitable instrumentation and electrical source known in the art capable of transmitting low electrical current.

According to some embodiments, the positive electrical current is delivered through a positive electrode placed on at least one site on the scrotum. The corresponding negative electrode may be placed anywhere else as long as patient compliance is maintained. A power source for inducing an electrical current is also included. The power source is preferably light, safe and may be integrated in a wearable device.

According to some embodiments, the positive electrode is external, though in other embodiments, the positive electrode may be internal, implanted inside the scrotum.

According to some embodiments, the positive electrode comprises a plurality of positive electrodes.

The electrodes may be conductive foils, wires or meshes and optionally may be covered on one or both sides with an insulating layer. The electrodes may be disposable. The electrodes may be coated with platinum black and steroid dexamethasone sodium phosphate to overcome corrosion. Preferably, the electrodes are electrically connected to a power supply, but insulated from the subject. The power supply set up may further include an automatic shutoff, capable of limiting the duration of the field administration as well as the magnitude of the electric current.

Any apparatus or otherwise set up that is used for conducting positive electric current based on the method of the invention may further include a feature capable of continuously monitoring the application of the desired electric current. Such feature should include one or more of the following: means for indicating the presence and magnitude of the electric current; means for indicating continuity of the current and means for indicating battery charge level where applicable. The apparatus may further include a regulatory system for regulating the current. The apparatus may further include means for controlling or adjusting the amplitude, timing and an interval program. The adjustment may be done automatically or manually by the user or by a medical caregiver. The apparatus is capable of performing under humidity, moisture, sweat and the like during the duration of the treatment.

The beneficial physiological effects achieved by the methods of the invention are observed only when the strength of the electric field on the scrotum lies in a certain range, otherwise called the effective current. According to some embodiments, the effective current is within the range of 1 µA to 1,000 µA.

For external applications the positive electrode may be in the form of a patch. The patch may be disposable. For example, the positive electrode and optionally the negative electrode, may be in the form of a flexible, optionally, adhesive, dermal patch. The patch may have a top surface and a skin contacting bottom surface, such that, the electrode is disposed substantially coplanar on the skin contacting bottom surface. According to some embodiments, the patch further comprises means and/or arrangement intended to maintain the electrode in continuous contact with the at least one site at the scrotum. The patch may further include an internal flexible power source.

A current may be applied by an external current source through wireless transmission. Thus, a current source can be outside the subject's body, and out of contact with the subject's body.

According to some embodiments, for improving the contact between the source of positive current and the at least one location at the scrotum, the method further comprises removing pubic hair prior to contacting the scrotum with said electrical source.

According to some embodiments, the skin area in contact with the electrode(s) may optionally be coated with conductive gel or paste. The conductive gel is placed between the skin contact and the electrode. While the conductive gel is between the skin contact and the electrode, the electrode used with such a conductive gel is still considered to be in contact with the skin of the subject. Similarly, in embodiments having an adhesive on the skin contact to maintain the desired position of the electrode are also considered to be in contact with the skin despite the presence of an adhesive layer on the skin contact surface.

According to some embodiments, the electrically conductive gel includes carbon. The carbon may comprise carbon particles or carbon fibers, and/or the thermally conductive gel includes particles of at least one of aluminum oxide, aluminum nitride and boron nitride.

According to some embodiments, the electrically conductive gel is hydrogel.

According to some embodiments, the set up which is intended to apply a positive current at one or more sites of the scrotum, further includes a device capable of controlling and monitoring the electrical current being applied.

The at least one site of the scrotum may be any site. For example, the at least one site may be a site adjacent to or onto the rete tesis.

Where an internal electrode is used, then applying a positive current involves any procedure enabling implanting said positive electrode inside the scrotum.

According to some embodiments, the positive electrical current is applied for a time period of at least 12 hours.

According to some embodiments, the positive electrical current is applied for a time period of at least 24 hours. According to some embodiments, the positive electrical current is applied for a time period of at least 36 hours. According to some embodiments, the positive electrical current is applied for at least 48 hours. According to some embodiments, the positive electrical current is applied for a time period of at least 7 days, According to some embodiments, the positive electrical current is applied for a time period of at least 30 days. According to some embodiments, the positive electrical current is applied for a time period of at least 60 days. According to some embodiments, the positive electrical current is applied for a time period of at least 74 days.

It is to be understood that the sperm sample, or one or more sperm samples, may be derived from said subject at various time points during treatment, namely, before completing application of said positive DC current. In addition or alternatively, the sperm sample, or one or more sperm samples, may be derived after the time period of applying the current is completed, including, but not limited to, a few minutes or hours thereafter, or days, weeks or months after applying the current is completed. According to some embodiments, said sperm sample is derived from said subject within at least one hour after the time period of applying the current is completed. According to some embodiments, said sperm sample is derived from said subject within 1 to 72 hours after the time period of applying the current is completed. According to some embodiments, said sperm sample is derived from said subject within 1 to 74 days after the time period of applying the current is completed. According to some embodiments, said sperm sample is derived from said subject at most 74 days after the time period of applying the current is completed. The derived sperm sample, or one or more sperm samples, maybe analyzed in order to determine whether or not treatment should be continued or in order to determine when to derive the next sample. Such determination may include evaluating sperm characteristics, including, but not limited to, quality and/or quantity. In a non-limiting example, for a sample having a sperm count of less than 15 million/ml, treatment may be continued and/or another sample should be derived and assessed following 5 to 74 days after treatment. In another non-limiting example, for a sample having a sperm count of about 20 million per milliliter, treatment may be continued and/or another sample should be derived and assessed following 5 to 24 days after treatment. In yet another non-limiting example, a sample having a sperm count of about 40 million/ml, may be used for assisted reproductive technologies and/or another sample should be derived and assessed following 2 to 24 days after treatment.

According to some embodiments, the method of the invention further comprises applying fertility treatments, during, before or after the application of the weak positive DC electric current. Each possibility represents a separate embodiment of the invention.

Fertility treatments depend on the underlying medical conditions that may be contributing to fertility problems and include, but are not limited to, drug therapy, hormonal therapy and surgery aimed to correct any obstructions in the reproductive tract.

According to some embodiments, the method of the invention is particularly useful in obtaining an improved semen sample in terms of quality and/or count of the sperm. As demonstrated herein below, by applying a positive current at a particular site of the scrotum, sperms are immobilized and concentrated at the site where the positive electric current was applied or at close vicinity to that site. Hence a sperm sample may be derived from a locus at the vicinity of the site subjected to positive current and then used for assisted reproductive techniques.

According to some embodiments, the method of the invention further comprises deriving a semen sample, and using said sample in a subsequent Assisted Reproductive Technique (ART).

According to some embodiments, the subject is non-human.

The present invention provides a method that can be utilized for improvement of methods for artificial insemination, including inseminating animals. The improvement comprises applying the method of the invention for upgrading the quality of the semen sample by, inter alia, increasing spermatocyte count characteristics and increasing spermatocyte productive capacity prior to utilization of the sample in artificial reproductive techniques. A major goal of fertilization processes, especially in patients with oligozoospermia or azoospermia is to increase spermatocyte count prior to fertilization. Thus, combining the method of the present invention with artificial reproductive techniques could result with higher success rates. Thus, the present invention offers higher probability of successful induction of pregnancy in infertile couples in which the male is the factor of infertility, both male and female are the cause of infertility or the cause of infertility is unknown.

The method of the invention for improving fertility also offers higher probability of success in spontaneous intercourse among men with normal sperm count.

As used herein the term "obtaining a semen sample" refers to any one or more of collecting, deriving, extracting or aspirating a semen sample from a scrotum of a male subject according to the method of the invention.

As used herein the term "semen" is interchangeable with the term "seminal fluid" and refers to an organic fluid that may contain sperm. In humans, seminal fluid contains several components besides sperm, such as proteolytic and other enzymes as well as fructose. All those components are essential for the vitality of sperm.

Obtaining a semen sample according to the method of the invention may be carried out during the treatment or after completion of the treatment, that is, after applying a DC positive electrical current for the amount of time required to achieve the desired sperm count, for example, at most 74 days after completion of the treatment.

According to some embodiments, applying said current is performed throughout a first time period, during which treatment may be paused at least once where during that pause a sperm sample is derived. The sperm sample may be analyzed to determine whether treatment should be continued. The analysis includes assessment of sperm characteristics, such as, sperm count and sperm capacity. Upon completion of said first time period, at least one sperm sample is obtained on one or more occasions during a second time period. According to some embodiments, the second time period is at most 74 days.

According to some embodiments, the desired sperm count is the maximal sperm count.

According to some embodiments, the treatment is applied until the sperm count reaches the maximal sperm count. According to some embodiments, the sperm count reaches maximum during treatment or during the period of up to 74 days after treatment was completed.

Obtaining a semen sample may be carried out according to any method or technique known in the art. Various methods for obtaining a semen sample are known and used according to the species of the animals. For example, a massage method, an electrical stimulation method, a hydraulic pressure method, and an artificial vagina method are mostly utilized in animals. In humans obtaining a semen sample may be carried out via a Testicular Sperm Aspiration (TESA), a Testicular Sperm Extraction (TESE) technology, Percutaneous Epididymal Sperm Aspiration (PESA), Microsurgical Epididymal Sperm Aspiration (MESA) or ejaculate.

According to some embodiments, a semen sample may be obtained or collected from any location within the scrotum of a subject including testis or epididymis. In cases where a positive electrode is utilized to deliver the positive electrical current, the semen sample may be obtained from a vicinity of the location where the positive electrode is placed.

According to some embodiments, the male subject in need thereof is a male subject diagnosed as infertile or subfertile. Each possibility represents a separate embodiment of the invention.

Generally, a total sperm count of less than approximately 40 million/ejaculate, which is defined as the product of ejaculate volume and sperm density, or alternatively a sperm concentration of less than 15 million/ml, with adequate motility and morphology, is considered to be a low sperm count and males exhibiting such characteristics are considered to be oligozoospermic. Oligozoospermia is considered to be severe when sperm count is lower than 5 million/ml.

According to some embodiments, the infertility or subfertility are due to poor semen characteristics which may be caused by various factors, including, but not limited to, sperm abnormalities and a range of conditions, such as anatomical problems, hormonal imbalances and genetic defects.

Sperm abnormalities may be characterized by abnormal sperm production with shape or motile defects or normal production with an abnormally low sperm number or seemingly without any sperm.

According to some embodiments, the infertile or subfertile condition is selected from the group consisting of: oligozoospermia, astenozoospermia, teratozoospermia and azoospermia. Each possibility represents a separate embodiment of the invention.

Azoospermia is the medical condition of males not having any measurable level of sperm in their semen. It is associated with very low levels of fertility or even sterility and affects 1% of the male population and 20% of male infertility situations. Over 50% of azoospermic cases are due to testicular failure including absence or failed production as well as low production and maturation arrest during the process of spermatogenesis. Males with non-obstructive azoospermia have 0 to 3 mature spermatids per seminiferous tubule in contrast to 17-35 mature spermatids in men with normal spermatogenesis.

Astenozoospermia refers to spermatozoa of very weak mobility or none at all. Teratozoospermia refers to a spermocytogram with less than 40% normal sperm. Parvisemia refers to an ejaculate volume of less than 2 ml. Germinal epithelium failure refers to a disorder of mammals that exhibit oligozoospermia as described above and yet have intact Leydig cell steroidogenic capacity and pituitary function. Such males have normal testosterone levels but low or non-existent sperm counts. Germinal epithelium failure is subcategorized to partial germinal epithelium failure and complete germinal epithelium failure.

According to some embodiments, the present invention provides a kit comprising a first component capable of applying an external positive electric current to at least one site of the scrotum of a male subject, said current is within the range of 1 µA to 1,000 µA, thereby improving fertility of said male subject.

According to some embodiments, the kit further comprises a second component capable of regulating, monitoring and/or adjusting the positive electrical current.

According to some embodiments, the kit further comprises instructions for use of said first component for improving fertility in a male subject.

According to some embodiments, the means capable of applying a positive electrical current to at least one site of the scrotum of a male subject, comprises a pair of electrodes and a power source.

According to some embodiments, the means capable of applying a positive electrical current is capable of applying the positive current in a continuous form, in intervals and/or pulses.

According to some embodiments, the means capable of applying a positive electrical current is capable of applying a continuous positive current.

According to some embodiments, the means capable of applying a positive electrical current is capable of applying the positive current in intervals.

According to some embodiments, the means capable of applying a positive electrical current is capable of applying the positive current for at least 12 hours, for at least 24 hours, for at least 72 hours, for at least 7 days, for at least 14 days, for at least 21 days, for at least 30 days, for at least 45 days, for at least 60 days or for at most 74 days. Each possibility is a separate embodiment of the invention.

According to some embodiments, said applying is carried out for 10 to 74 days.

According to some embodiments, the kit further comprises means for deriving a sperm sample from a subject.

According to some embodiments, the kit further comprises means for deriving a sperm sample from a subject by aspiration, extraction or ejaculation.

According to some embodiments, the kit further comprises means for determining a sperm characteristics selected from the group consisting of: total sperm count, sperm concentration, ejaculate volume, sperm motility, sperm morphology and sperm viability.

It is to be understood that the method of the invention includes non-invasive steps for improving male fertility. Similarly, the kit of the invention includes non-invasive means for improving male fertility.

Specifically, the positive electric current applied in the course of the method of the invention is low, below sensation levels, safe and thereby can be applied for days, weeks or even months. In some embodiments, the current is applied for 72 days.

In addition to the exemplary aspects and embodiments described above, further aspects and embodiments will become apparent by reference to the figures and by study of the following examples. The materials, methods and examples discussed below are illustrative and are not intended to limit the scope of the invention.

EXAMPLES

Example 1: The Effect of Low Positive Current on Spermatocyte Count

A positive electrical current of 40 µA was applied internally onto the right testicle of two male pigs (treatment group) using lithium batteries as a power source. The negative electrode was applied internally close by on the testis. The left testicle remained untreated and served as control. The experiment was conducted for 12 days after which several sperm samples from various locations in proximity to the location of the positive electrode that provided the current were obtained and cell count was performed.

Figure 2A:
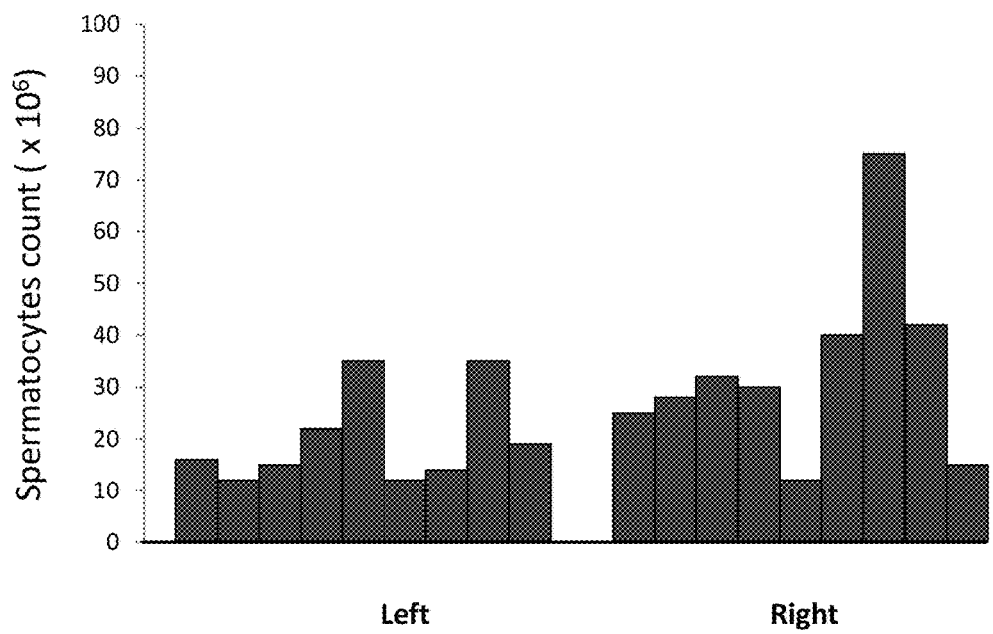
FIGS. 2A and 2B present bar graphs indicating spermatocytes count (in millions) in two (A and B) male pigs. Samples were obtained from a plurality of sites of the right testis after electrodes were implanted on this testis and positive electrical current of 40 µAm was continuously applied for 12 days; in comparison to the left testis (control) where no current was delivered.
Figure 2B:
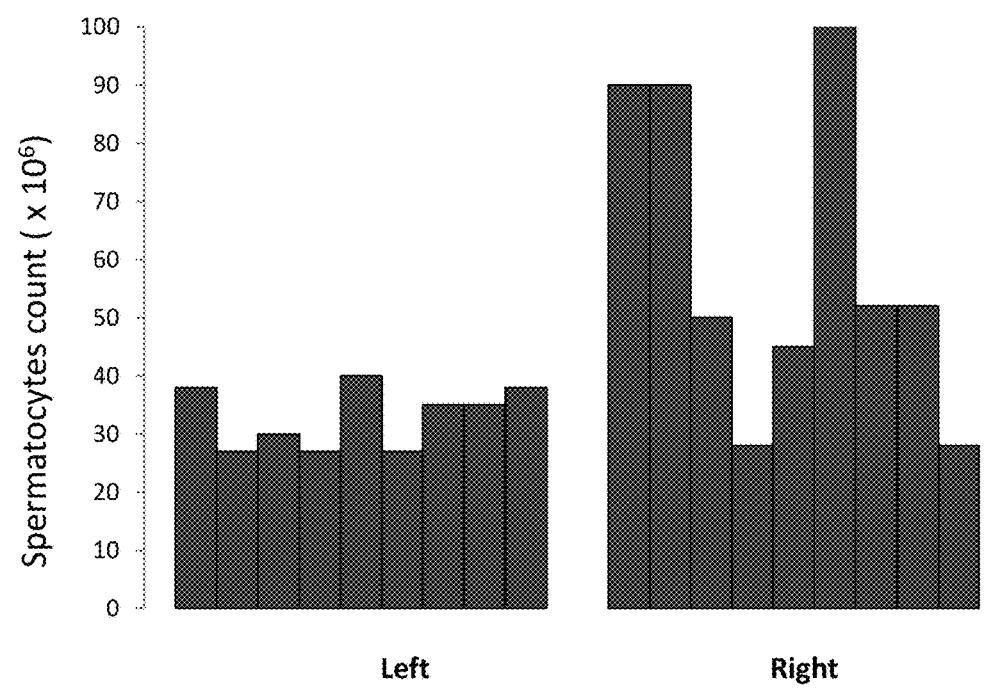

The average cell count in the control left testis of the first animal (FIG. 2A) was $20 \times 10^6$, while the average cell count in the right testis following treatment was $33 \times 10^6$. In another animal (FIG. 2B) the average cell count in the control left testis was $33 \times 10^6$, while the average cell count in the right testis following treatment was $61 \times 10^6$ (p=0.01).

The results indicate that low positive electrical current increases spermatocyte count in a significant manner.

Example 2: The Topical Effect of Low Positive Current

Figure 3:
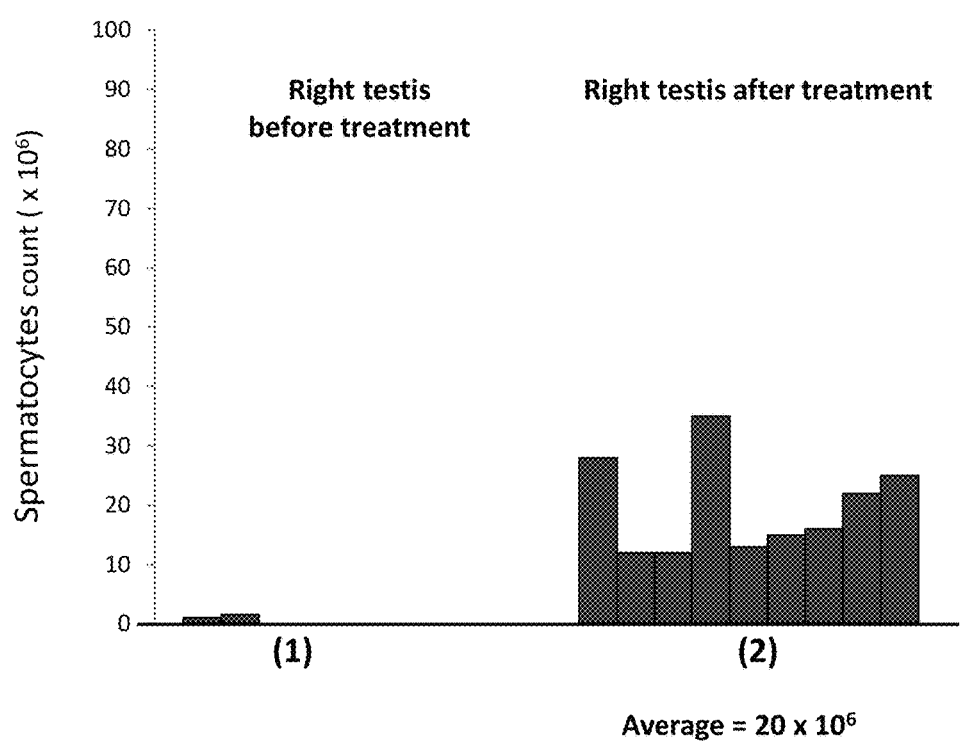
FIG. 3 is a bar graph indicating spermatocytes count (in millions) in male pigs of samples obtained from the right testis before (1) and after (2) testis was subjected to 12 days topical application of positive electrical current of 100 µAm.

A positive electrical current of 100 µA was applied externally onto the right scrotum of a male pig using lithium batteries as a power source. The negative electrode was applied at a further location on the animal's back. The experiment was conducted for 12 days (FIG. 3).

Spermatocyte count was evaluated before treatment (1) and at the end of treatment at a plurality of sites (2).

Prior to treatment, the animal was found to be oligozoospermic. The results indicate low spermatocyte count ($1.25 \times 10^6$) in (1) before treatment in comparison to a significant sperm count ($20 \times 10^6$) in (2) after treatment.

The results indicate that low positive electrical current increases spermatocyte count in a significant manner.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A method for improving male fertility comprising
generating a positive electric current within the range of 10 µA to 500 µA from a power source; and
contacting at least one site of the scrotum of a male subject with at least one positive electrode connected to said current; and
applying, prior to intercourse, the positive electric current to the at least one site thereby improving male fertility towards induction of pregnancy via natural intercourse.

2. The method of claim 1, wherein said at least one site is an external site in close proximity to the rete testis.

3. The method of claim 1, wherein said applying is carried out for at least 12 hours prior to intercourse.

4. The method of claim 1, further comprising determining infertility in said male subject, prior to said applying the positive current to at least one site of the scrotum of a male having an infertility condition.

5. The method of claim 1, wherein improving male fertility comprises improving one or more of sperm count, sperm quality, sperm concentration, ejaculate volume, sperm motility, sperm morphology, sperm viability and sperm reproductive capacity.

6. The method of claim 1, wherein said male subject is infertile or subfertile.

7. The method of claim 1, further comprising treating the male subjects with fertility treatments during, before or after said applying the positive current.

8. The method of claim 1, wherein said male subject is having a normal sperm count.

9. The method of claim 1, wherein said subject is not a human subject.

10. The method of claim 1, wherein the power source is a lithium battery.

11. The method of claim 1, wherein the positive electric current is within the range of 10 µA to 400 µA.

12. An assisted reproductive method comprising:
a. generating a positive electric current within the range of 10 µA to 500 µA from a power source;
b. contacting at least one site of the scrotum of a male subject with at least one positive electrode thereby applying the positive current to the at least one site;
c. obtaining at least one sperm sample from said male subject after step (b); and
d. performing an assisted reproductive technique using said at least one sample.

13. The method of claim 12, wherein obtaining said at least one semen sample from said subject is carried out at most 74 days after said applying the positive electric current.

14. The method of claim 12, wherein said subject is not a human subject.

15. The method of claim 12, wherein the power source is a lithium battery.

16. The method of claim 12, wherein said at least one semen sample is derived from a location selected from a group consisting of: at the vicinity of said at least one site, a testis, an epididymis and via ejaculation.

* * * * *